(12) United States Patent
Takasu

(10) Patent No.: US 11,371,925 B2
(45) Date of Patent: Jun. 28, 2022

(54) MEASUREMENT APPARATUS FOR MEASURING MASS CONCENTRATION OF PARTICLES USING CORRELATION OF NUMBER CONCENTRATION, HUMIDITY AND CONCENTRATION AND MEASUREMENT METHOD FOR MEASURING MASS CONCENTRATION OF PARTICLES USING CORRELATION OF NUMBER CONCENTRATION, HUMIDITY AND CONCENTRATION

(71) Applicant: FUJITSU LIMITED, Kawasaki (JP)

(72) Inventor: Ryozo Takasu, Isehara (JP)

(73) Assignee: FUJITSU LIMITED, Kawasaki (JP)

( * ) Notice: Subject to any disclaimer, the term of this patent is extended or adjusted under 35 U.S.C. 154(b) by 501 days.

(21) Appl. No.: 16/451,670

(22) Filed: Jun. 25, 2019

(65) Prior Publication Data
US 2019/0317003 A1 Oct. 17, 2019

Related U.S. Application Data

(63) Continuation of application No. PCT/JP2017/046675, filed on Dec. 26, 2017.

(30) Foreign Application Priority Data

Jan. 13, 2017 (JP) .............................. JP2017-004618

(51) Int. Cl.
*G01N 15/06* (2006.01)
*G01N 33/00* (2006.01)
*G01N 15/00* (2006.01)

(52) U.S. Cl.
CPC ........... *G01N 15/06* (2013.01); *G01N 33/004* (2013.01); *G01N 33/0037* (2013.01);
(Continued)

(58) Field of Classification Search
CPC .............. G01N 15/06; G01N 33/0037; G01N 33/0039; G01N 33/004; G01N 33/0042;
(Continued)

(56) References Cited

U.S. PATENT DOCUMENTS

2015/0346071 A1* 12/2015 Takasu ............... G01N 15/0606
73/28.01
2016/0349168 A1* 12/2016 Takasu ............... G01N 15/1459
2017/0315105 A1* 11/2017 Takeda ............... G01N 33/0042

FOREIGN PATENT DOCUMENTS

CN          105300861 A      2/2016
EP          3 214 429 A1     9/2017
(Continued)

OTHER PUBLICATIONS

International Search Report dated Apr. 10, 2018, issued in counterpart International Application No. PCT/JP2017/046675 (1 page).
(Continued)

*Primary Examiner* — David Z Huang
(74) *Attorney, Agent, or Firm* — WHDA, LLP

(57) ABSTRACT

A measurement apparatus includes: a number concentration measurement device configured to measure a number concentration of particles in a air; a humidity measurement device configured to measure a humidity of the air; and a air concentration measurement device configured to measure a concentration of a specific air in the air, wherein a mass concentration of the particles in the air is calculated based on a measured number concentration, a measured humidity, a measured concentration of the specific air, and a predetermined correlation between the number concentration, the humidity, and the concentration of the specific air, and the mass concentration of the particles in the air.

14 Claims, 15 Drawing Sheets

(52) U.S. Cl.
CPC ..... *G01N 33/0039* (2013.01); *G01N 33/0042* (2013.01); *G01N 33/0044* (2013.01); *G01N 33/0047* (2013.01); *G01N 2015/0046* (2013.01); *G01N 2015/0693* (2013.01)

(58) Field of Classification Search
CPC .......... G01N 33/0044; G01N 33/0047; G01N 2015/0046; G01N 2015/0693; Y02A 50/20
See application file for complete search history.

(56) References Cited

FOREIGN PATENT DOCUMENTS

| JP | 11-281757 A | 10/1999 |
|---|---|---|
| JP | 2000-180348 A | 6/2000 |
| JP | 2009-75004 A | 4/2009 |
| JP | 2015-224962 A | 12/2015 |
| JP | 2016-223907 A | 12/2016 |
| WO | 2016/067484 A1 | 5/2016 |

OTHER PUBLICATIONS

Lin et al., "Research on Influencing Factors of PM2.5 Concentration", Annual Conference of Chinese Society for Environmental Sciences, Oct. 14, 2016, pp. 2681-2687, cited in CN Office Action dated Apr. 27, 2021. (8 pages).

Wu et al., "Effect of Ammonium Sulfate Aerosol on the Photochemical Reaction of Toluene/NOx/Air Mixture", Environmental Science, Jun. 2007, vol. 28, No. 6, pp. 1183-1187, cited in CN Office Action dated Apr. 27, 2021. (5 pages).

Office Action dated Apr. 27, 2021, issued in counterpart CN application No. 201780082945.4, with English translation. (18 pages).

* cited by examiner

FIG. 7A

| CONVERSION FUNCTION |
|---|
| f (h,c) |

FIG. 7B

| GAS CONCENTRATION | CONVERSION FUNCTION |
|---|---|
| c1 | fa (h) |
| c2 | fb (h) |
| c3 | fc (h) |
| ⋮ | ⋮ |

FIG. 7C

| | | GAS CONCENTRATION | | | |
|---|---|---|---|---|---|
| | | c1 | c2 | c3 | ... |
| HUMIDITY | h1 | Cn/Cm11 | Cn/Cm21 | Cn/Cm31 | ... |
| | h2 | Cn/Cm12 | Cn/Cm22 | Cn/Cm32 | ... |
| | h3 | Cn/Cm13 | Cn/Cm23 | Cn/Cm33 | ... |
| | ⋮ | ⋮ | ⋮ | ⋮ | ⋮ |

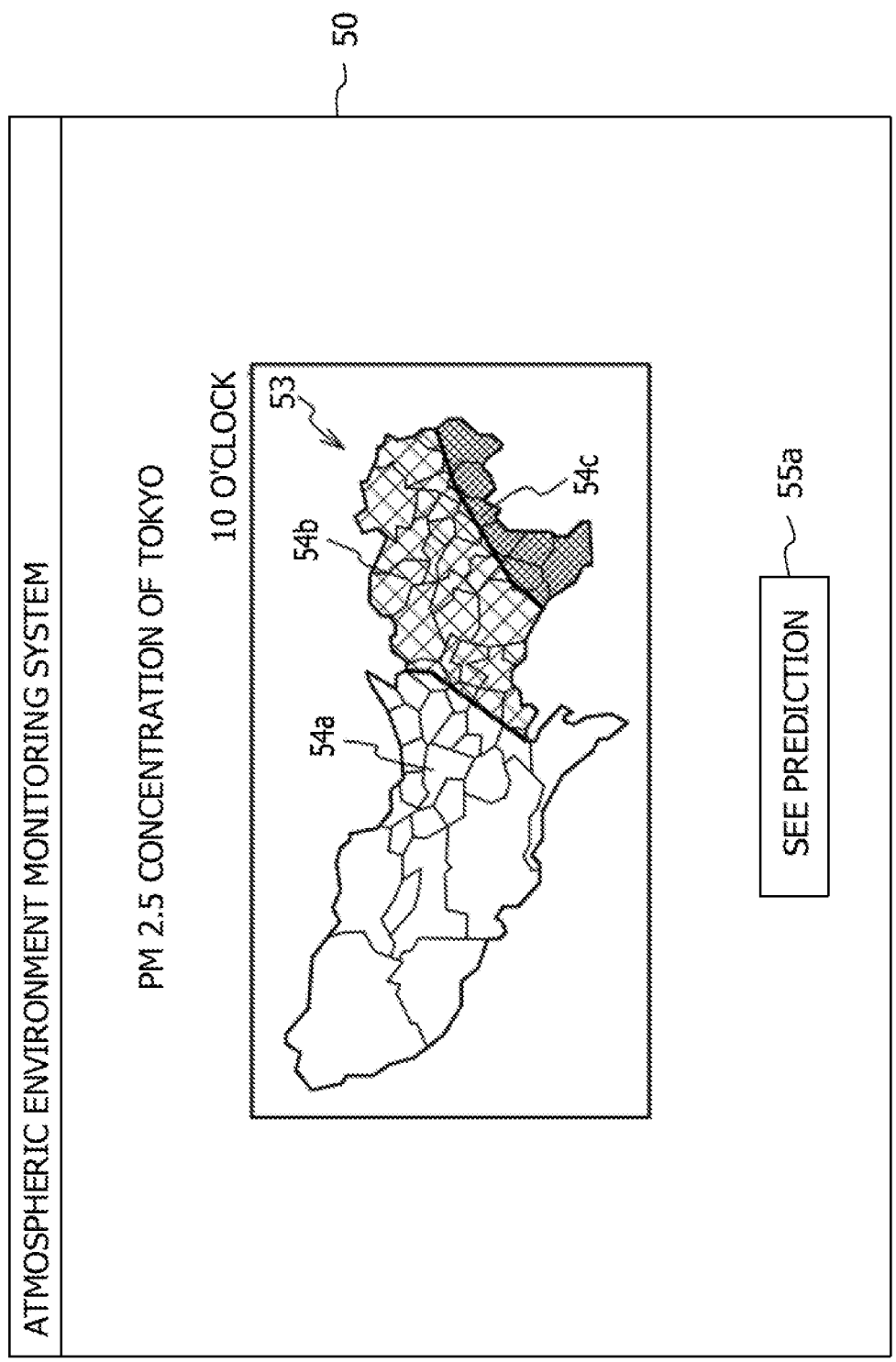

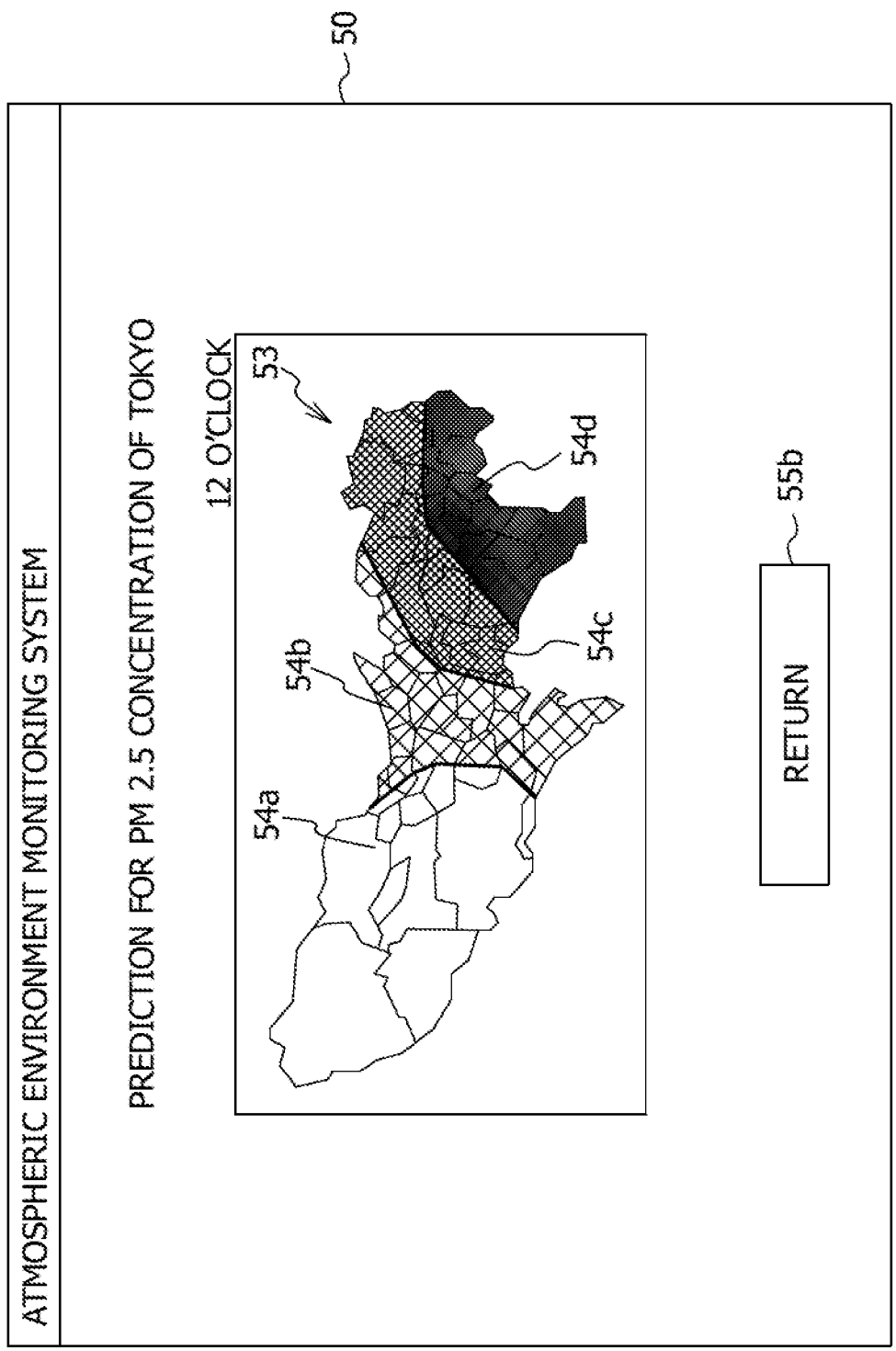

MEASUREMENT APPARATUS FOR MEASURING MASS CONCENTRATION OF PARTICLES USING CORRELATION OF NUMBER CONCENTRATION, HUMIDITY AND CONCENTRATION AND MEASUREMENT METHOD FOR MEASURING MASS CONCENTRATION OF PARTICLES USING CORRELATION OF NUMBER CONCENTRATION, HUMIDITY AND CONCENTRATION

CROSS-REFERENCE TO RELATED APPLICATION

This application is a continuation application of International Application PCT/JP2017/046675 filed on Dec. 26, 2017 and designated the U.S., the entire contents of which are incorporated herein by reference. The International Application PCT/JP2017/046675 is based upon and claims the benefit of priority of the prior Japanese Patent Application No. 2017-004618, filed on Jan. 13, 2017, the entire contents of which are incorporated herein by reference.

FIELD

The embodiments relate to a measurement apparatus and a measurement method.

BACKGROUND

In recent years, the concentration of a particulate matter such as PM 2.5 in air has been actively measured.
Related art is disclosed in Japanese Laid-open Patent Publication No. 2015-224962

SUMMARY

According to an aspect of the embodiments, a measurement apparatus includes: a number concentration measurement device configured to measure a number concentration of particles in a air; a humidity measurement device configured to measure a humidity of the air; and a air concentration measurement device configured to measure a concentration of a specific air in the air, wherein a mass concentration of the particles in the air is calculated based on a measured number concentration, a measured humidity, a measured concentration of the specific air, and a predetermined correlation between the number concentration, the humidity, and the concentration of the specific air, and the mass concentration of the particles in the air.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIGS. 7A to 7C are diagrams illustrating a conversion function stored in a storage unit in the first embodiment.

FIG. 14 is a diagram (No. 2) illustrating an example of a screen of an information processing terminal.

FIG. 15 is a diagram (No. 3) illustrating an example of a screen of an information processing terminal.

DESCRIPTION OF EMBODIMENTS

Figure 1:
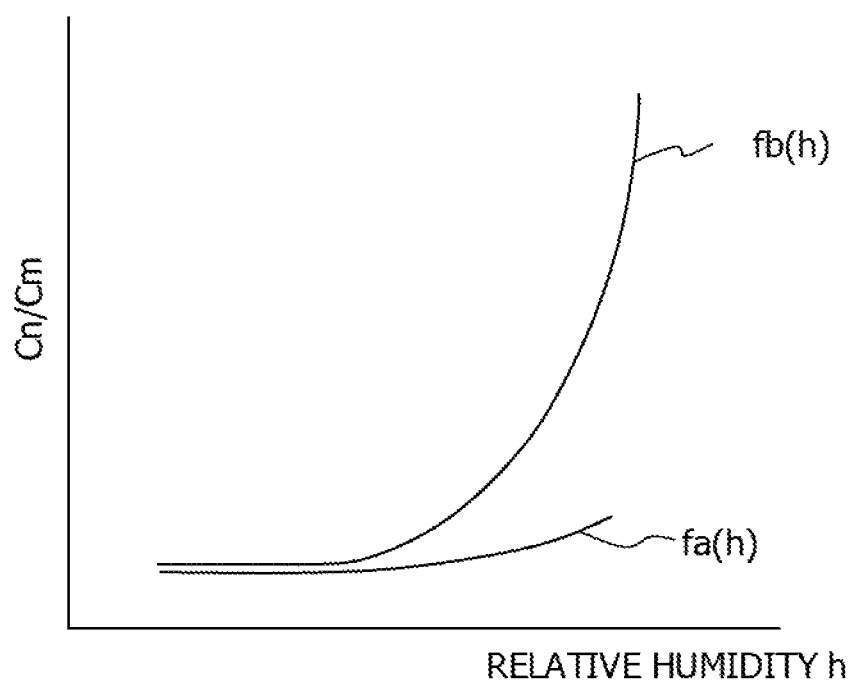
FIG. 1 is a graph illustrating a conversion coefficient Cn/Cm with respect to a relative humidity in particles having low hygroscopicity and particles having high hygroscopicity.

As a unit of the concentration of particles in a gas, the mass of particles contained in a gas per unit volume is used (for example, $mg/m^3$ or $\mu g/m^3$). This particle concentration is referred to as a mass concentration. Examples of a standard measurement method of the mass concentration of PM 2.5 include a method for collecting particles in a gas into a filter and measuring the mass thereof. In addition, there is a beta ray attenuation method as a measurement method of a mass concentration capable of automatic measurement. The concentration obtained by the filter method or the beta ray attenuation method is a mass concentration, and the concentration of PM 2.5 is expressed by the mass concentration. Examples thereof further include, as an inexpensive and simple method, a light scattering detection method for measuring the number of particles per unit volume (for example, $number/m^2$) in a gas by scattered light obtained by irradiating the particles in the gas with light. A number concentration is measured by a simple method, and a mass concentration is calculated based on the number concentration and a humidity using a correlation formula between the mass of particles and the humidity.

By using the correlation formula between the mass of particles and a humidity, the number concentration of particles can be measured using an inexpensive and simple light scattering detection method, and the number concentration can be converted into a mass concentration. However, a conversion coefficient that converts the number concentration into the mass concentration differs depending on a component of the particles. The component of the particles changes temporally or spatially. For this reason, when the number concentration is converted into the mass concentration using a constant conversion coefficient, the accuracy of the mass concentration is low. Therefore, a conversion coefficient that converts the number concentration into the mass concentration is calculated at a certain frequency spatially or temporally. For example, a measurement apparatus that calculates a correlation between the mass of particles and a humidity is large and expensive.

For example, the measurement apparatus and measurement method may aim to reduce size or cost.

Some of particles such as PM 2.5 are secondary particles. The secondary particles are particles generated by a chemical reaction of a gas serving as a precursor. In addition, there are particles having high hygroscopicity and particles having low hygroscopicity depending on a component of particles. Examples of a component having high hygroscopicity include ammonium sulfate $(NH_4)_2SO_4$, ammonium nitrate $NH_4NO_3$, sodium chloride NaCl, sodium sulfate $Na_2SO_4$, and sodium nitrate $NaNO_3$. Examples of a component having low hygroscopicity include elemental carbon, a water-insoluble organic substance, and a soil component. Among these components, examples of a component of secondary particles include ammonium sulfate, ammonium nitrate, sodium sulfate, and sodium nitrate. Elemental carbon may be generated as secondary particles but is not necessarily in a form of secondary particles, for example, in a case of dust. Sodium chloride is a component mainly derived from seawater.

Examples of a precursor gas of ammonium sulfate include hydrogen sulfide $H_2S$, ammonia $NH_3$, sulfur dioxide $SO_2$, and ozone $O_3$. Examples of a precursor gas of ammonium nitrate include nitrogen monoxide NO, ammonia $NH_3$, nitrogen dioxide $NO_2$, and ozone $O_3$. Examples of a precursor gas of sodium sulfate include hydrogen sulfide $H_2S$, sulfur dioxide $SO_2$, and ozone $O_3$. Examples of a precursor gas of sodium nitrate include nitrogen monoxide NO, nitrogen dioxide $NO_2$, and ozone $O_3$. Examples of a precursor gas of elemental carbon include CO and volatile organic compounds (VOCs). A chemical reaction from a precursor gas to secondary particles is complicated.

FIG. 1 is a graph illustrating a conversion coefficient Cn/Cm with respect to a relative humidity in particles having low hygroscopicity and particles having high hygroscopicity. Cn/Cm is a ratio of a number concentration Cn with respect to a mass concentration Cm and is function f(h) of a relative humidity h. Once function f(h) is determined, Cn/f(h) becomes a mass concentration Cm using the measured number concentration Cn. As illustrated in FIG. 1, in particles having low hygroscopicity, Cn/Cm hardly changes even if relative humidity h changes, as in fa(h). In particles having high hygroscopicity, Cn/Cm increases as relative humidity h increases, as in fb(h). For example, fa(h) is a conversion function when a component of particles is elemental carbon, and fb(h) is a conversion function when a component of particles is ammonium nitrate.

For example, a case where particles mainly contain elemental carbon such as dust and ammonium nitrate which is in a form of secondary particles is considered. In this case, a conversion function is between fa(h) and fb(h) depending on a ratio between elemental carbon particles and ammonium nitrate particles. The conversion function approaches fa(h) if the amount of elemental carbon particles increases, and the conversion function approaches fb(h) if the amount of ammonium nitrate particles increases.

The concentration of particles mainly containing elemental carbon such as dust is hardly affected by a specific gas concentration. A mechanism of generation of particles mainly containing ammonium nitrates is complicated. For example, a reaction in which $NH_4NO_3$ is generated from $NO_2$ and $NH_3$, a reaction in which $NO_2$ is generated from NO and $O_3$, and a reaction in which decomposition occurs contrary to these reactions are conceivable. For example, if it is considered that $NO_2$ is mainly rate-limiting for generation of $NH_4NO_3$, it is considered that the concentration of ammonium nitrate particles depends on an $NO_2$ concentration. Therefore, a relationship between the $NO_2$ concentration and conversion function f(h) is predetermined.

Figure 2:
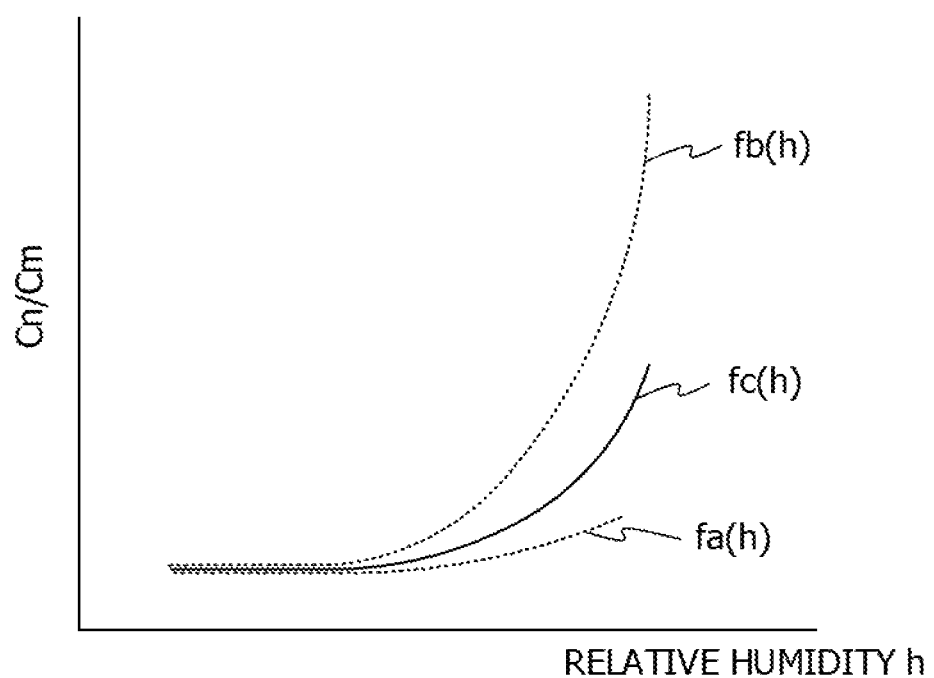
FIG. 2 is a graph illustrating a conversion coefficient Cn/Cm with respect to a relative humidity at a certain gas concentration.

FIG. 2 is a graph illustrating a conversion coefficient Cn/Cm with respect to a relative humidity at a certain gas concentration ($NO_2$ concentration). As illustrated in FIG. 2, if the $NO_2$ concentration is known, conversion function fc(h) is determined. This makes it possible to convert a number concentration into a mass concentration. A chemical reaction depends on a temperature, the amount of ultraviolet light, and a pressure. For example, if these values are large, a reaction is likely to proceed. For example, if it is considered that a temperature most affects generation of ammonium nitrate particles, it is considered that conversion function fc(h) in FIG. 2 changes with the temperature. Therefore, a relationship between the temperature and conversion function fc(h) is predetermined.

Figure 3:
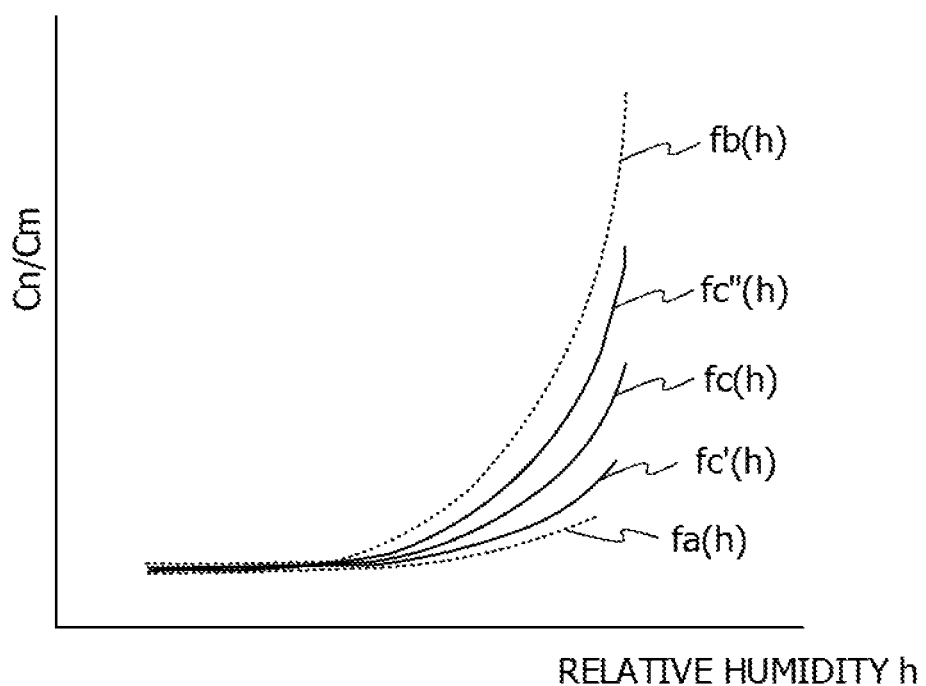
FIG. 3 is a graph illustrating a conversion coefficient Cn/Cm with respect to a relative humidity at a certain temperature.

FIG. 3 is a graph illustrating a conversion coefficient Cn/Cm with respect to a relative humidity at a certain temperature. As illustrated in FIG. 3, for example, if it is assumed that a reaction of generation of ammonium nitrate particles proceeds when the temperature is high, fc" (h) is used instead of conversion function fc(h) when the temperature is high. When the temperature is low, fc' (h) is used instead of fc(h). This makes it possible to convert a number concentration into a mass concentration more accurately.

Figure 4:
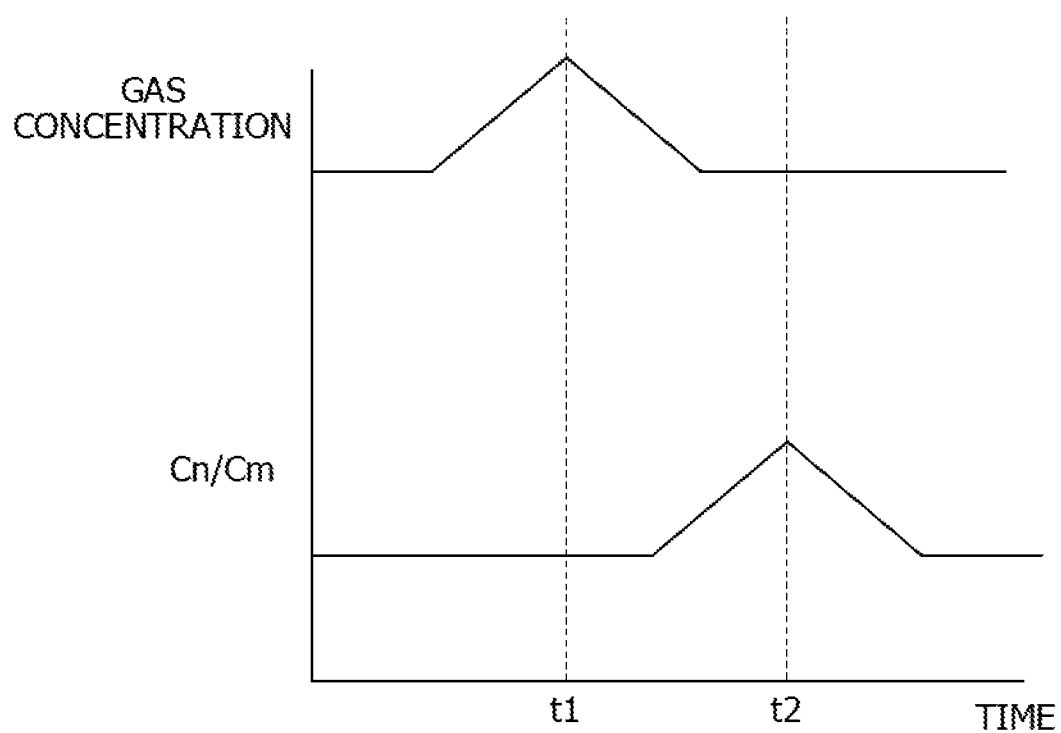
FIG. 4 is a graph illustrating time dependency of a gas concentration and a conversion coefficient Cn/Cm.

FIG. 4 is a graph illustrating time dependency of a gas concentration and a conversion coefficient Cn/Cm. It takes time for secondary particles to be generated. Therefore, as illustrated in FIG. 4, there may be a time difference between time t1 at which the gas concentration peaks and time t2 at which the conversion coefficient Cn/Cm peaks. In such a case, as a gas concentration for calculating conversion function f(h), a value a period of a time difference t2−t1 before the measurement time is used. This makes it possible to measure a mass concentration accurately.

Based on the above, embodiments will be described.

First Embodiment

Figure 5:
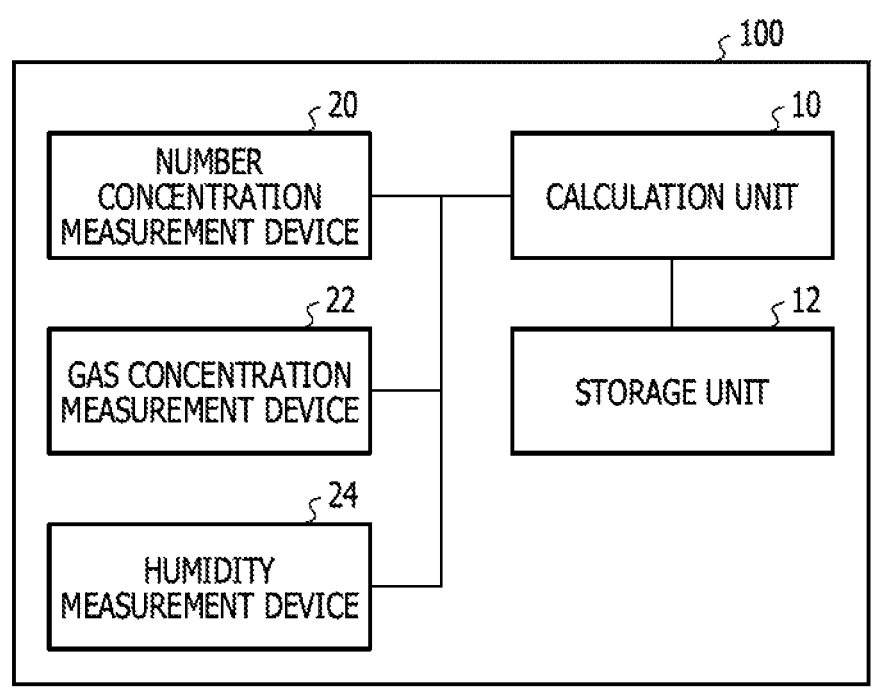
FIG. 5 is a block diagram of a measurement apparatus according to a first embodiment.

FIG. 5 is a block diagram of a measurement apparatus according to a first embodiment. As illustrated in FIG. 5, a measurement apparatus 100 includes a calculation unit 10, a storage unit 12, a number concentration measurement device 20, a gas concentration measurement device 22, and a humidity measurement device 24. The calculation unit 10 is, for example, a processor or a computer, and calculates a mass concentration with a program. The calculation unit 10 may be a dedicated circuit. The storage unit 12 is, for example, a non-volatile memory such as a flash memory or a hard disk unit, and stores a relationship of f(h) with respect to a gas concentration. The number concentration measurement device 20 is, for example, a number concentration measurement device according to a light scattering detection method, and measures the number concentration of particles such as PM 2.5 in a gas. The gas concentration measurement device 22 is, for example, a gas sensor, and measures the concentration of a specific gas in a gas. One gas concentration measurement device 22 may be disposed to measure the concentration of one type of gas. A plurality of gas concentration measurement devices 22 may be disposed to measure the concentrations of a plurality of gases. For example, a gas sensor to measure the concentration of at least one gas of $H_2S$, NO, $NH_3$, $NO_2$, $SO_2$, $O_3$, CO, and VOCs only needs to be disposed. The humidity measurement device 24 measures, for example, a relative humidity in a gas.

Figure 6:
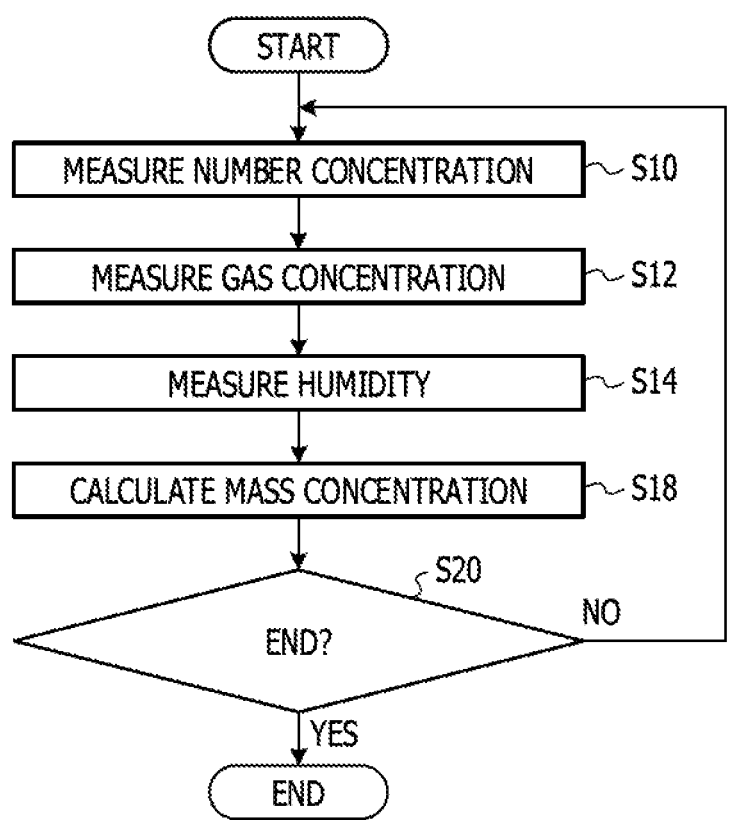
FIG. 6 is a flowchart illustrating a measurement method according to the first embodiment.

FIG. 6 is a flowchart illustrating a measurement method according to the first embodiment. As illustrated in FIG. 6, the number concentration measurement device 20 measures the number concentration of particles in a gas (step S10). The gas concentration measurement device 22 measures the concentration of a specific gas in a gas containing particles (step S12). The humidity measurement device 24 measures a relative humidity in a gas containing particles (step S14). The calculation unit 10 calculates the mass concentration of particles in a gas based on the measured number concentration, the measured gas concentration, and the measured humidity (step S18). The calculation unit 10 outputs the calculated mass concentration. The calculation unit 10 judges whether to end the measurement of the mass concentration (step S20). If yes, the measurement ends. If no, the process returns to step S10. The order of steps S10 to S14 can be set arbitrarily. In addition, a time interval at which step S10 to S18 are performed can be set arbitrarily. The number concentration, the gas concentration, and the humidity may be measured almost simultaneously, but may be measured at different times.

Step S18 will be described in detail. FIGS. 7A to 7C are diagrams illustrating a conversion function stored in a storage unit in the first embodiment. As illustrated in FIG. 7A, the storage unit 12 stores conversion function f(h, c) which is a conversion coefficient Cn/Cm with a humidity h and a gas concentration c as variables. The calculation unit 10 acquires conversion function f(h, c) from the storage unit 12. The calculation unit 10 substitutes the gas concentration c measured in step S12 and the humidity h measured in step S14 into conversion function f(h, c) to calculate a conversion coefficient Cn/Cm. A mass concentration Cm is calculated based on the number concentration Cn measured in step S10 and the conversion coefficient Cn/Cm.

As illustrated in FIG. 7B, the storage unit 12 stores conversion functions fa (h), fb (h), fc (h) . . . corresponding to gas concentrations c1, c2, c3 . . . . The calculation unit 10 acquires conversion function fi(h) corresponding to the measured gas concentration ci from the storage unit 12. The calculation unit 10 substitutes the measured humidity h into conversion function fi(h) to calculate a conversion coefficient Cn/Cm. A mass concentration Cm is calculated based on the measured number concentration Cn and the conversion coefficient Cn/Cm.

As illustrated in FIG. 7C, the storage unit 12 stores a table indicating conversion coefficients Cn/Cm11, Cn/Cm12, Cn/Cm13, . . . corresponding to gas concentrations c1, c2, c3 . . . and humidities h1, h2, h3 . . . . The calculation unit 10 acquires a conversion coefficient Cn/Cmij corresponding to the measured gas concentration ci and the measured humidity hj from the storage unit 12. The calculation unit 10 calculates a mass concentration Cm based on the measured number concentration Cn and the conversion coefficient Cn/Cmij.

When a mass concentration is calculated from gas concentrations ca, cb, cc . . . of a plurality of gases, in FIG. 7A, the storage unit 12 stores conversion functions f(h, ca, cb, cc . . . ) with respect to a humidity h and concentrations ca, cb, cc . . . . In the case of FIG. 7B, the storage unit 12 stores conversion functions f(h) corresponding to concentrations ca, cb, cc . . . . The calculation unit 10 acquires conversion functions f(h) corresponding to concentrations ca, cb, cc . . . from the storage unit 12. In the case of FIG. 7C, the storage unit 12 stores values of Cn/Cm corresponding to a humidity h and concentrations ca, cb, cc, . . . as a table. The calculation unit 10 acquires values of Cn/Cm corresponding to a humidity h and concentrations ca, cb, cc, . . . from the storage unit 12.

According to the first embodiment, the calculation unit 10 calculates the mass concentration of particles in a gas based on the measured number concentration, the measured humidity, and the measured concentration of a specific gas, and a predetermined correlation between the number concentration, the humidity, and the concentration of the specific gas, and the mass concentration in the gas. As a result, as described with reference to FIG. 2, a conversion coefficient Cn/Cm can be accurately calculated. Therefore, a mass concentration can be calculated accurately. In addition, a gas sensor that measures the concentration of a specific gas is small and inexpensive. As a result, a number concentration can be accurately converted into a mass concentration without using a large and expensive measurement apparatus that measures a correlation between the mass of particles and a humidity or the like. Therefore, a small and inexpensive measurement apparatus can be provided.

Examples of a precursor gas that generates secondary particles include $H_2S$, NO, $NH_3$, $NO_2$, $SO_2$, $O_3$, CO, and VOCs. Therefore, the specific gas to be measured for the gas concentration thereof is at least one gas of $H_2S$, NO, $NH_3$, $NO_2$, $SO_2$, $O_3$, CO, and VOCs. This makes it possible to measure a mass concentration accurately.

The number concentration measurement device 20 measures a number concentration using a light scattering detection method. This makes it possible to measure a number concentration inexpensively.

As illustrated in FIGS. 7A and 7B, the storage unit 12 stores a function of a mass concentration in a gas with respect to a number concentration, a humidity, and the concentration of a specific gas. The calculation unit 10 calculates the mass concentration of particles in a gas based on the measured number concentration, the measured humidity, the measured concentration of a specific gas, and the stored function. This makes it possible to calculate the mass concentration.

As illustrated in FIG. 7C, the storage unit 12 stores a table illustrating a mass concentration in a gas corresponding to a number concentration, a humidity, and the concentration of a specific gas. The calculation unit 10 calculates the mass concentration of particles in a gas based on the measured number concentration, the measured humidity, the measured concentration of a specific gas, and the table. This makes it possible to calculate the mass concentration.

Second Embodiment

Figure 8:
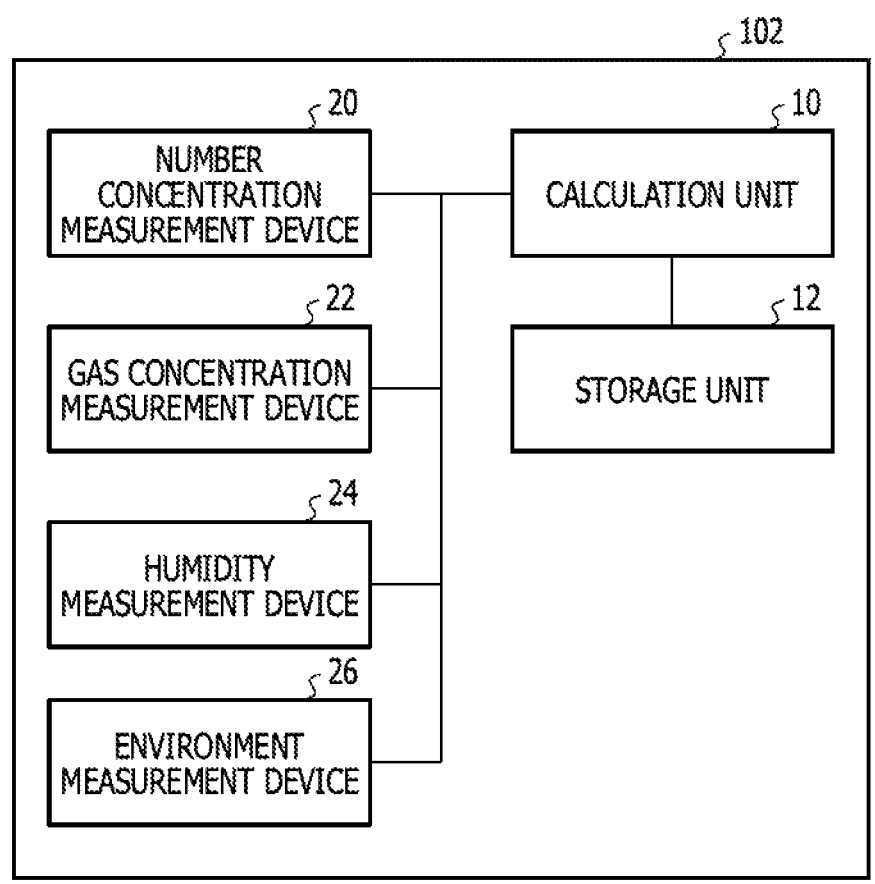
FIG. 8 is a block diagram of a measurement apparatus according to a second embodiment.

FIG. 8 is a block diagram of a measurement apparatus according to a second embodiment. As illustrated in FIG. 8, a measurement apparatus 102 includes an environment measurement device 26. The environment measurement device 26 measures environmental information that is at least one of the amount of ultraviolet light irradiated to a gas, the temperature of the gas, and the pressure of the gas. When the environment measurement device 26 measures the amount of ultraviolet light, the environment measurement device 26 is an ultraviolet light meter. When the environment measurement device 26 measures the temperature, the environment measurement device 26 is a thermometer. When the environment measurement device 26 measures the pressure, the environment measurement device 26 is a barometer. The other configuration is the same as that of the first embodiment, and description thereof will be omitted.

Figure 9:
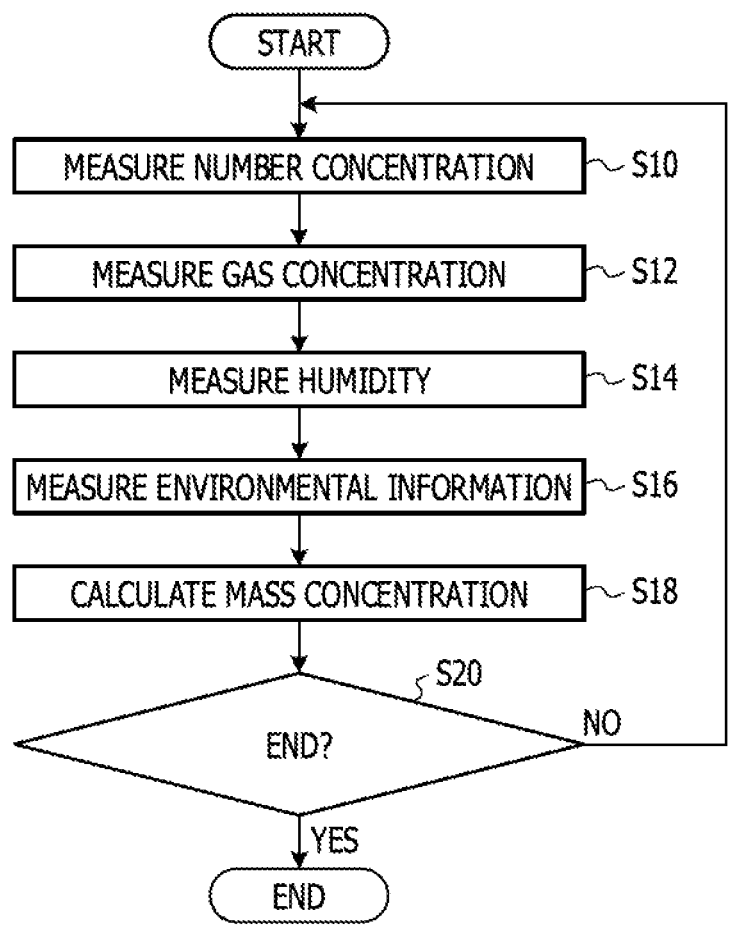
FIG. 9 is a flowchart illustrating a measurement method according to the second embodiment.

FIG. 9 is a flowchart illustrating a measurement method according to the second embodiment. As illustrated in FIG. 9, the environment measurement device 26 measures environmental information between steps S14 and S18 (step S16). The environment measurement device 26 measures at least one of the amount of ultraviolet light, a temperature, and a pressure. The order of steps S10 to S16 can be set arbitrarily. The number concentration, the gas concentration, the humidity, and the environmental information may be measured almost simultaneously, but may be measured at different times. The other flow is the same as that in the first embodiment, and description thereof will be omitted.

According to the second embodiment, as a correlation for calculating the mass concentration, the calculation unit 10 uses the measured number concentration, the measured humidity, the measured concentration of a specific gas, and the measured environmental information, and a predetermined correlation between the number concentration, the humidity, the concentration of the specific gas, and the environmental information, and the mass concentration in the gas. A reaction of a precursor gas is affected by at least one of the amount of ultraviolet light, a temperature, and a pressure. Therefore, as described in FIG. 3, the mass concentration can be accurately calculated by correcting a conversion coefficient with the environmental information.

In the second embodiment, as in FIGS. 7A and 7B, the storage unit 12 stores a function of a mass concentration in a gas with respect to a number concentration, a humidity, the concentration of a specific gas, and environmental information. The calculation unit 10 may calculate the mass concentration of particles in a gas based on the measured number concentration, the measured humidity, the measured concentration of a specific gas, the measured environmental information, and the stored function. This makes it possible to calculate the mass concentration.

In addition, as in FIG. 7C, the storage unit 12 stores a table illustrating a mass concentration in a gas corresponding to a number concentration, a humidity, the concentration of a specific gas, and environmental information. The calculation unit 10 may calculate the mass concentration of particles in a gas based on the measured number concentration, the measured humidity, the measured concentration of a specific gas, the measured environmental information, and the table. This makes it possible to calculate the mass concentration.

Third Embodiment

Figure 10:
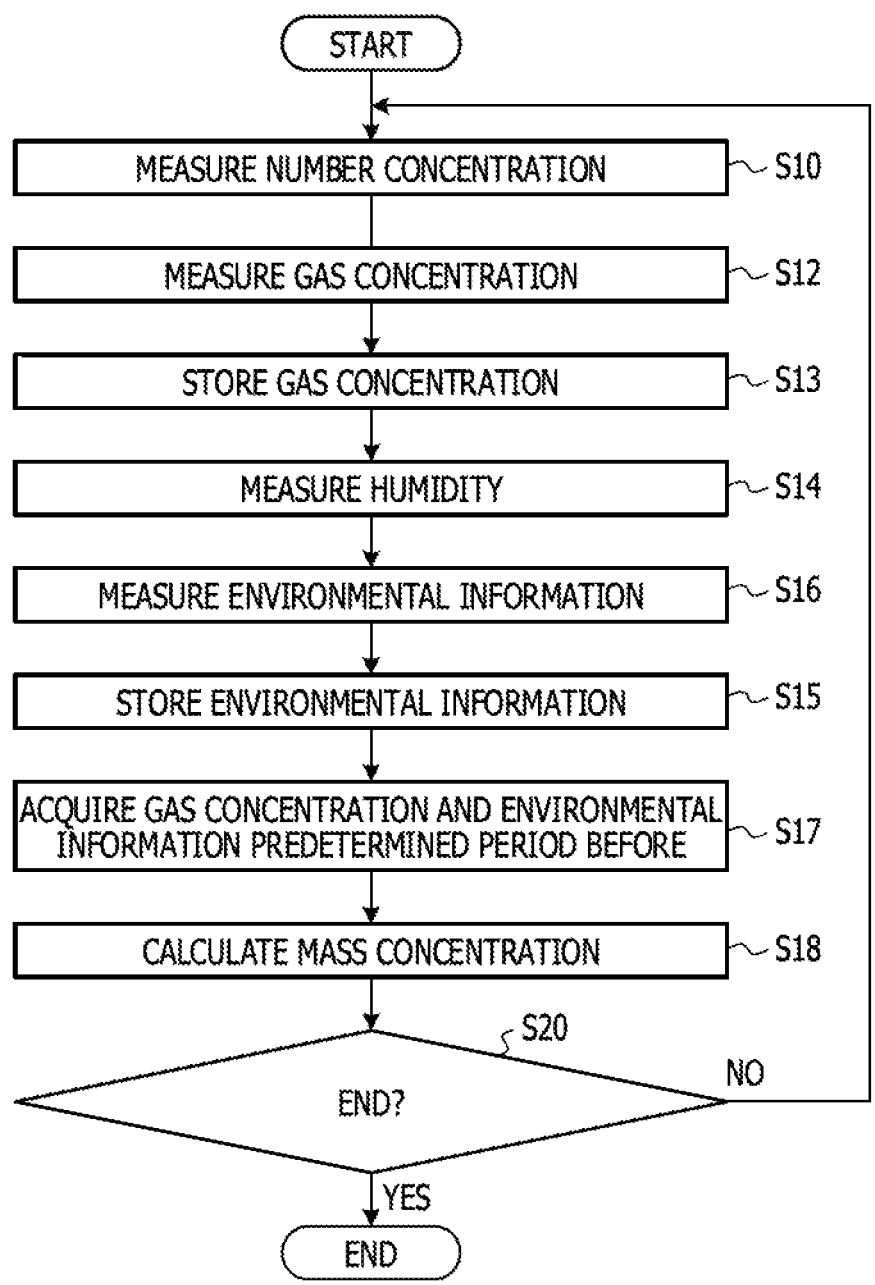
FIG. 10 is a flowchart illustrating a measurement method according to a third embodiment.

FIG. 10 is a flowchart illustrating a measurement method according to a third embodiment. As illustrated in FIG. 10, after step S12, the storage unit 12 stores the measured gas concentration in association with the measured time (step S13). After step S16, the storage unit 12 stores the measured environmental information in association with the measured time (step S15). Before step S18, the calculation unit 10 acquires a gas concentration and/or environmental information corresponding to a time which is a predetermined period before the time when the number concentration is measured (step S17). The calculation unit 10 calculates a mass concentration based on the gas concentration and/or the environmental information a predetermined period before the measurement time acquired from the storage unit 12 and the measured number concentration and humidity (step S18). The other configuration is the same as that of the second embodiment, and description thereof will be omitted.

According to the third embodiment, the calculation unit 10 calculates a mass concentration using, as the concentration of a specific gas, the concentration of the specific gas measured a predetermined period before the time when the measured number concentration and humidity are measured. As a result, as illustrated in FIG. 4, even when there is a time difference between the gas concentration and the conversion coefficient Cn/Cm, the mass concentration can be calculated accurately.

In addition, the calculation unit 10 may calculate the mass concentration using, as environmental information, the environmental information measured a predetermined period before the time when the measured number concentration and the measured humidity are measured. In these cases, the predetermined periods for the gas concentration and the environmental information may be the same as or different from each other. When the calculation unit 10 uses the gas concentrations of a plurality of gases, the predetermined periods for the plurality of gases may be the same as or different from one another. When the calculation unit 10 uses a plurality of pieces of environmental information, the predetermined periods for the plurality of pieces of environmental information may be the same as or different from one another.

Figure 11:
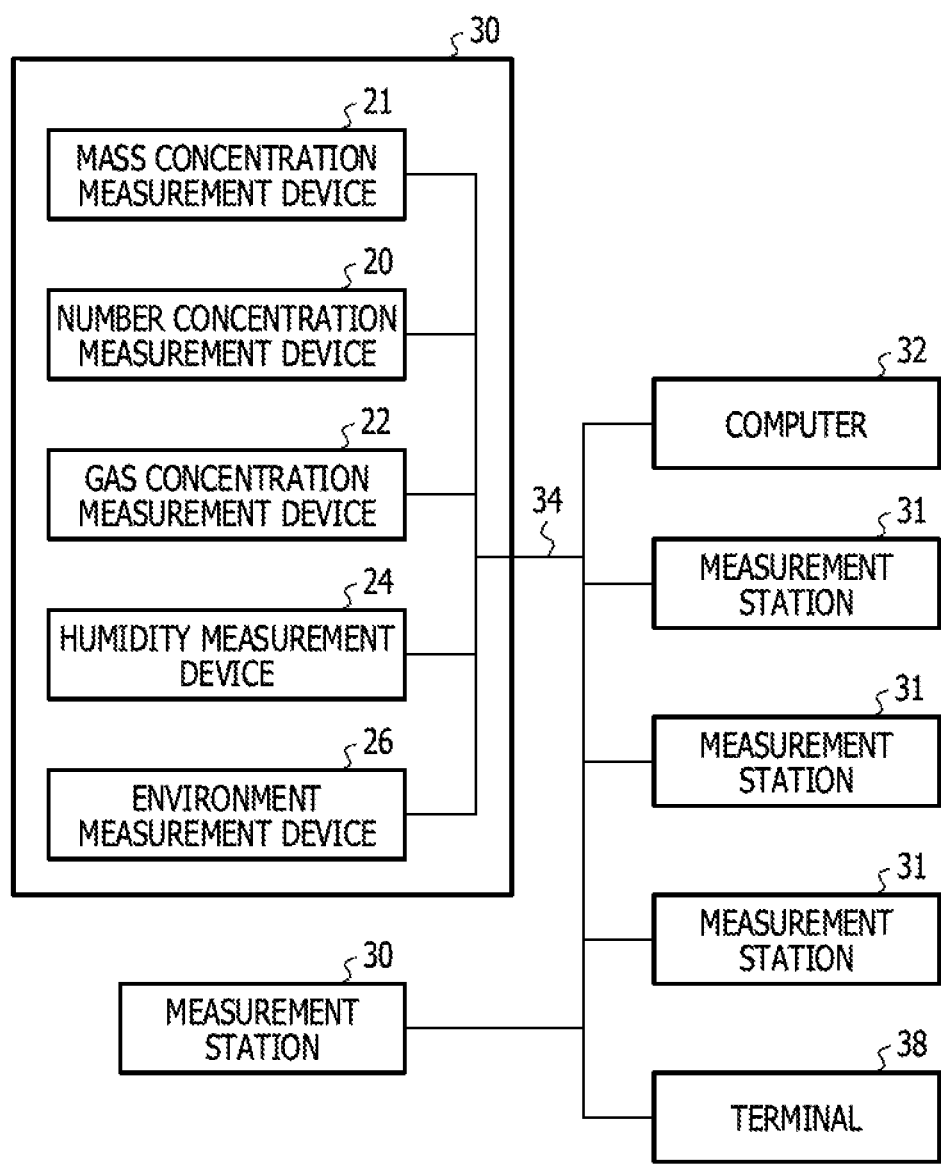
FIG. 11 is a diagram illustrating a system in the first to third embodiments.

FIG. 11 is a diagram illustrating a system in the first to third embodiments. As illustrated in FIG. 11, a computer 32, a plurality of measurement stations 30, a plurality of measurement stations 31, and a terminal 38 are connected to a network 34. The network 34 includes wired and/or wireless networks. Each of the measurement stations 30 includes a number concentration measurement device 20, a mass concentration measurement device 21, a gas concentration measurement device 22, a humidity measurement device 24, and an environment measurement device 26. The mass concentration measurement device 21 is, for example, a measurement device using a beta ray attenuation method, and measures the mass concentration of particles in a gas at each of the measurement stations 30. The functions of the other measurement devices are the same as those in the first to third embodiments. Each of the measurement stations 31 does not include the mass concentration measurement device 21 and is, for example, the measurement apparatus 100 or 102 according to the first to third embodiments. The terminal 38 is an information processing terminal used by a user who uses the system, such as a computer or a portable terminal.

Figure 12A:
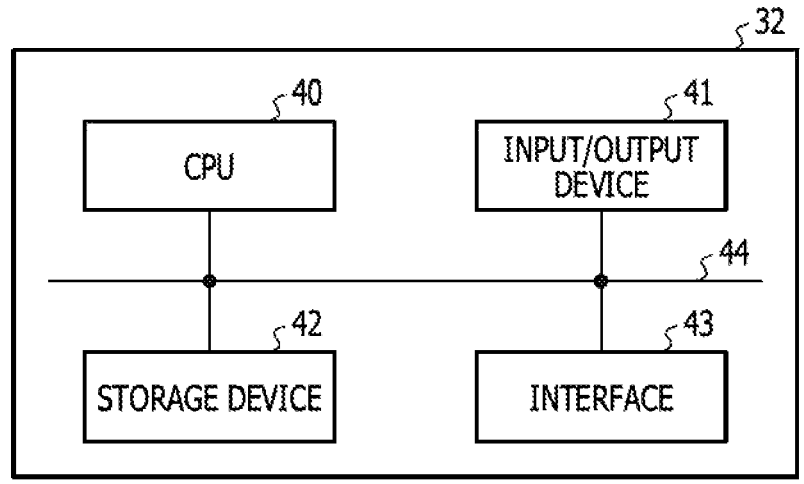
FIG. 12A is a block diagram of a computer.
Figure 12B:
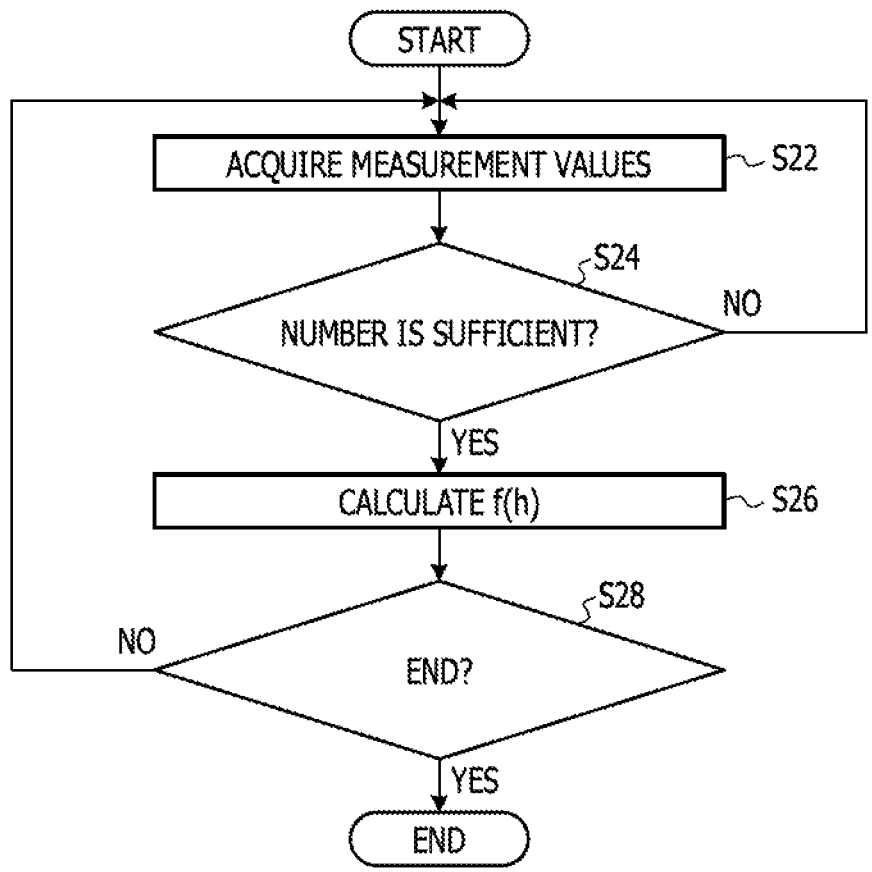
FIG. 12B is a flowchart illustrating processing performed by a processor in the computer.

FIG. 12A is a block diagram of a computer, and FIG. 12B is a flowchart illustrating processing performed by a processor in the computer. As illustrated in FIG. 12A, the computer 32 includes a central processing unit (CPU) 40, an input/output device 41, a storage device 42, an interface 43, and an internal bus 44. The input/output device 41 is a display device such as a liquid crystal panel and/or an input device such as a keyboard, a mouse, or a touch panel. The storage device 42 is a volatile memory and/or a non-volatile memory, and stores a program and data that is being processed or has been processed. The interface 43 inputs/outputs data with the measurement stations 30 and 31 and the terminal 38 via the network 34. The internal bus 44 connects devices in the computer 32.

As illustrated in FIG. 12B, a processor such as the CPU 40 acquires measured values such as the mass concentration, the number concentration, the gas concentration, the humidity, and the environmental information measured almost simultaneously from each of the measurement stations 30 (step S22). For example, the CPU 40 acquires each measurement value at regular intervals (for example, one hour). The CPU 40 stores the mass concentration, the number concentration, the gas concentration, the humidity, and the environmental information measured at almost the same time as one set in the storage device 42. The CPU 40 judges whether a sufficient number of pieces of data has been collected in order to calculate a correlation (step S24). If No, the process returns to step S22. If Yes, the CPU 40 statistically processes the collected mass concentration, the collected number concentration, the collected humidity, the collected gas concentration, and the collected environmental information, and calculates conversion function f(h) corresponding to the gas concentration and/or the environmental information (step S26). For example, as illustrated in FIGS. 2 and 3, fc(h), fc' (h), or fc" (h) with respect to a certain gas concentration and/or certain environmental information is calculated. The CPU 40 stores the calculated f(h) in the storage device 42. The CPU 40 judges whether the process ends (step S28). For example, if measurement of a concentration is stopped, the CPU 40 judges that it is yes. If Yes, the process ends. If No, the process returns to step S22. From the above, conversion function f(h) with respect to a gas concentration and/or environmental information can be calculated.

In order to reflect a difference in a component of particles, it is preferable to use measurement values of the measurement stations 30 disposed in various places (for example, a seaside area, a mountain village, and a factory area). When conversion function f(h) is calculated using a plurality of gas concentrations and/or a plurality of pieces of environmental information, the CPU 40 may use a method such as multivariate analysis or machine learning.

In the first to third embodiments, the calculation unit 10 and the storage unit 12 may be the CPU 40 of the computer 32 and the storage device 42 thereof, respectively. In this case, the CPU 40 acquires the measured number concentration, the measured humidity, the measured concentration of a specific gas, and the measured environmental information from each of the measurement stations 31. The CPU 40 calculates the mass concentration of particles in a gas based on the number concentration, the humidity, the concentration of a gas, and the environmental information acquired from the measurement stations 31, and a predetermined correlation between the number concentration, the humidity, the concentration of the specific gas, and the environmental information stored in the storage device 42, and the mass concentration in the gas. The calculation unit 10 and the storage unit 12 may also be included in a computer connected to the network 34 in addition to the computer 32.

The computer 32 may function as a data collecting server and/or a data delivering server. The interval at which each of the measurement stations 31 transmits the concentration of PM 2.5 to the computer 32 can be set arbitrarily. If a light scattering method is used for the measurement apparatuses 100 and 102, for example, the concentration of PM 2.5 can be transmitted at intervals of one second. In this way, the concentration of PM 2.5 can be collected in real time.

A user accesses the computer 32 using a web browser of the terminal 38. The computer 32 can provide a measurement value of the concentration of PM 2.5 from the stored data of the concentration of PM 2.5 in response to a request of the terminal 38. As the concentration of PM 2.5, it is possible to provide a real-time measurement value, a past measurement value of the concentration of PM 2.5, or an expected value of the concentration of PM 2.5.

Figure 13:
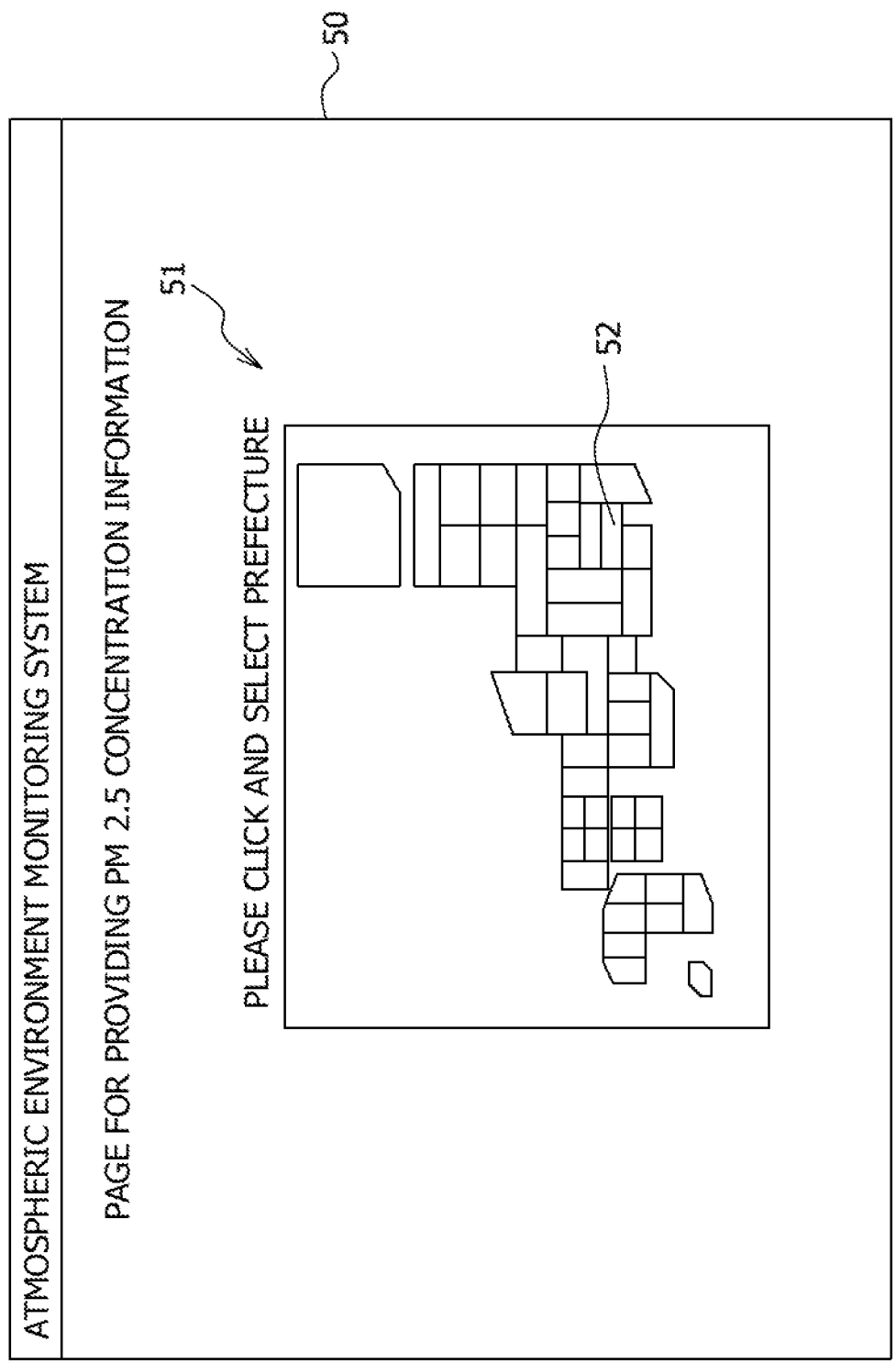
FIG. 13 is a diagram (No. 1) illustrating an example of a screen of an information processing terminal.

FIGS. 13 to 15 are diagrams illustrating examples of a screen of an information processing terminal. As illustrated in FIG. 13, when the computer 32 is accessed, a Japanese map 51 is displayed on a screen 50 of the terminal 38 as a page for providing PM 2.5 concentration information. On the screen 50, "Please click and select a prefecture" is described. A prefecture in the Japanese map 51 is clicked. For example, Tokyo 52 is clicked.

As illustrated in FIG. 14, a map 53 of Tokyo is displayed on the screen 50 of the terminal 38. The map 53 is color-coded into areas 54a to 54c corresponding to the concentration of PM 2.5 at ten o'clock. For example, the concentration of PM 2.5 is low in the area 54a, and the concentration of PM 2.5 is high in the area 54c. Below the map 53, a more detailed map hierarchy may be disposed. A banner 55a displaying "See prediction" is displayed on the screen. The banner 55a is clicked.

As illustrated in FIG. 15, the map 53 is color-coded into areas 54a to 54d corresponding to the concentration of PM 2.5 at 12 o'clock. The area 54d is a range in which the concentration of PM 2.5 exceeds a reference value. At 12 o'clock, it is found that the concentration of PM 2.5 is highly likely to exceed the reference value in some areas. A user in the area 54d can cope therewith, for example, the user avoids going outdoors. A banner 55b displaying "Return" is displayed on the screen. If the banner 55b is clicked, the screen returns to FIG. 14. The computer 32 can also deliver an alert to the terminal 38 of a user in an area where the concentration of PM 2.5 exceeds the reference value.

According to the first to third embodiments, the mass concentration of particles can be obtained by the small and inexpensive measurement apparatuses 100 and 102. This makes it easy to dispose many measurement stations 31 each including the measurement apparatus 100 or 102. The measurement stations 31 are connected to the computer 32 using the Internet. This makes it possible for a user to know the concentration of PM 2.5 in a desired area in real time using the terminal 38. Since a measurement interval of each of the measurement apparatuses 100 and 102 can be short, for example, one second, the trend of PM 2.5 in the atmosphere can be captured finely. This makes it possible to predict the concentration of PM 2.5. The concentration of PM 2.5 has been exemplified as the mass concentration of particles in FIGS. 13 to 15. However, the mass concentration of particles in the atmosphere other than the concentration of PM 2.5 can also be used.

Although the embodiments of the present invention have been described in detail thus far, the present invention is not limited to such specific embodiments, and various modifications and alterations may be made within the scope of the present invention described in the claims.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A measurement apparatus comprising:
    a number concentration measurement device configured to measure a number concentration of particles in an air;
    a humidity measurement device configured to measure a humidity of the air;
    an air concentration measurement device configured to measure a concentration of a specific air in the air; and a processor configured to calculate a mass concentration of the particles in the air based on a measured number concentration, a measured humidity, a measured concentration of the specific air, and a predetermined correlation between the number concentration, the humidity, and the concentration of the specific air, and the mass concentration of the particles in the air.

2. The measurement apparatus according to claim 1, wherein the specific air is at least one air of $H_2S$, NO, $NH_3$, $NO_2$, $SO_2$, $O_3$, CO, and VOCs.

3. The measurement apparatus according to claim 1, comprising:
an environment measurement device configured to measure at least one piece of environmental information of an amount of ultraviolet light which is irradiated to the air, a temperature of the air, and a pressure of the air,
wherein the predetermined correlation includes a correlation among the measured number concentration, the measured humidity, the measured concentration of the specific air and the measured environmental information, a predetermined number concentration, humidity, concentration of the specific air and environmental information, and the mass concentration in the air.

4. The measurement apparatus according to claim 1, wherein the measured concentration of the specific air is a concentration of the specific air which is measured a predetermined period before a time when the measured number concentration and the measured humidity are measured.

5. The measurement apparatus according to claim 1, wherein the processor is configured to calculate the mass concentration of the particles in the air based on the measured number concentration, the measured humidity, the measured concentration of the specific air, and the predetermined correlation.

6. The measurement apparatus according to claim 5, comprising:
a storage that stores a function of the mass concentration of the particles in the air with respect to the number concentration, the humidity, and the concentration of the specific air,
wherein the processor calculates the mass concentration of the particles in the air based on the measured number concentration, the measured humidity, the measured concentration of the specific air, and the function.

7. The measurement apparatus according to claim 5, comprising:
a storage that stores a table illustrating the mass concentration of the particles in the air corresponding to the number concentration, the humidity, and the concentration of the specific air,
wherein the processor calculates the mass concentration of the particles in the air based on the measured number concentration, the measured humidity, the measured concentration of the specific air, and the table.

8. The measurement apparatus according to claim 1, wherein the number concentration measurement device measures the number concentration using a light scattering detection method.

9. A measurement method comprising:
measuring a number concentration of particles in an air;
measuring a humidity of the air;
measuring a concentration of a specific air in the air; and
calculating a mass concentration of the particles in the air based on a measured number concentration, a measured humidity, a measured concentration of the specific air, and a predetermined correlation between the number concentration, the humidity, and the concentration of the specific air, and the mass concentration of the particles in the air.

10. The measurement method according to claim 9, wherein the specific air is at least one air of $H_2S$, NO, $NH_3$, $NO_2$, $SO_2$, $O_3$, CO, and VOCs.

11. The measurement method according to claim 9, comprising:
measuring at least one piece of environmental information of an amount of ultraviolet light which is irradiated to the air, a temperature of the air, and a pressure of the air,
wherein the predetermined correlation includes a correlation among the measured number concentration, the measured humidity, the measured concentration of the specific air and the measured environmental information, a predetermined number concentration, humidity, concentration of the specific air and environmental information, and the mass concentration in the air.

12. The measurement method according to claim 9, wherein the measured concentration of the specific air is a concentration of the specific air which is measured a predetermined period before a time when the measured number concentration and the measured humidity are measured.

13. The measurement method according to claim 9, comprising:
calculating the mass concentration of the particles in the air based on the measured number concentration, the measured humidity, the measured concentration of the specific air, and the predetermined correlation.

14. The measurement method according to claim 9, further comprising:
measuring the number concentration using a light scattering detection method.

* * * * *